US007340842B2

(12) United States Patent
Rabe

(10) Patent No.: US 7,340,842 B2
(45) Date of Patent: Mar. 11, 2008

(54) MEASURING BEDDING ARTICLES AND METHODS FOR MEASURING USING SAME

(76) Inventor: Jace B. Rabe, 507 Governors Cir., Roswell, GA (US) 30076

(*) Notice: Subject to any disclaimer, the term of this patent is extended or adjusted under 35 U.S.C. 154(b) by 0 days.

(21) Appl. No.: 11/503,758

(22) Filed: Aug. 14, 2006

(65) Prior Publication Data

US 2008/0034600 A1 Feb. 14, 2008

(51) Int. Cl.
*G01B 3/10* (2006.01)
*A47G 9/06* (2006.01)
(52) U.S. Cl. .............................. 33/512; 33/755; 5/420
(58) Field of Classification Search ................. 33/512, 33/562–563, 11–12, 755, 759–760, 768, 770, 33/679.1; 5/420, 482, 486, 499, 500, 502
See application file for complete search history.

(56) References Cited

U.S. PATENT DOCUMENTS 5,664,269 A * 9/1997 Broder .......................... 5/486

| 2005/0034317 A1* | 2/2005 | Burandt et al. ................ 33/512 |
| 2005/0204471 A1* | 9/2005 | Ruiz .............................. 5/420 |
| 2007/0240326 A1* | 10/2007 | Cerbelli et al. ................ 33/755 |

* cited by examiner

*Primary Examiner*—Yaritza Guadalupe-McCall
(74) *Attorney, Agent, or Firm*—Coursey IP Law, P.C.; R. Stevan Coursey, Esq.

(57) ABSTRACT

Measuring bedding articles and methods for measuring the length of a person's body or a portion thereof that enable such measurement while the person is lying down, thereby allowing the measuring of children or infants who cannot yet stand or the measuring of adults or adolescents who may be unable to stand for some reason. In some exemplary embodiments, the measuring bedding article comprises a measuring blanket or a measuring crib sheet. The measuring bedding article includes a measuring aid integral therewith and having end markings defining a distance therebetween, a plurality of markings between such end markings that define smaller distance increments, and a plurality of numerals that enable the making of measurements. The measuring article also includes a recordation label that allows multiple measurements and the corresponding dates thereof to be recorded for subsequent review and/or analysis that may be indicative of physical development or decline.

23 Claims, 8 Drawing Sheets

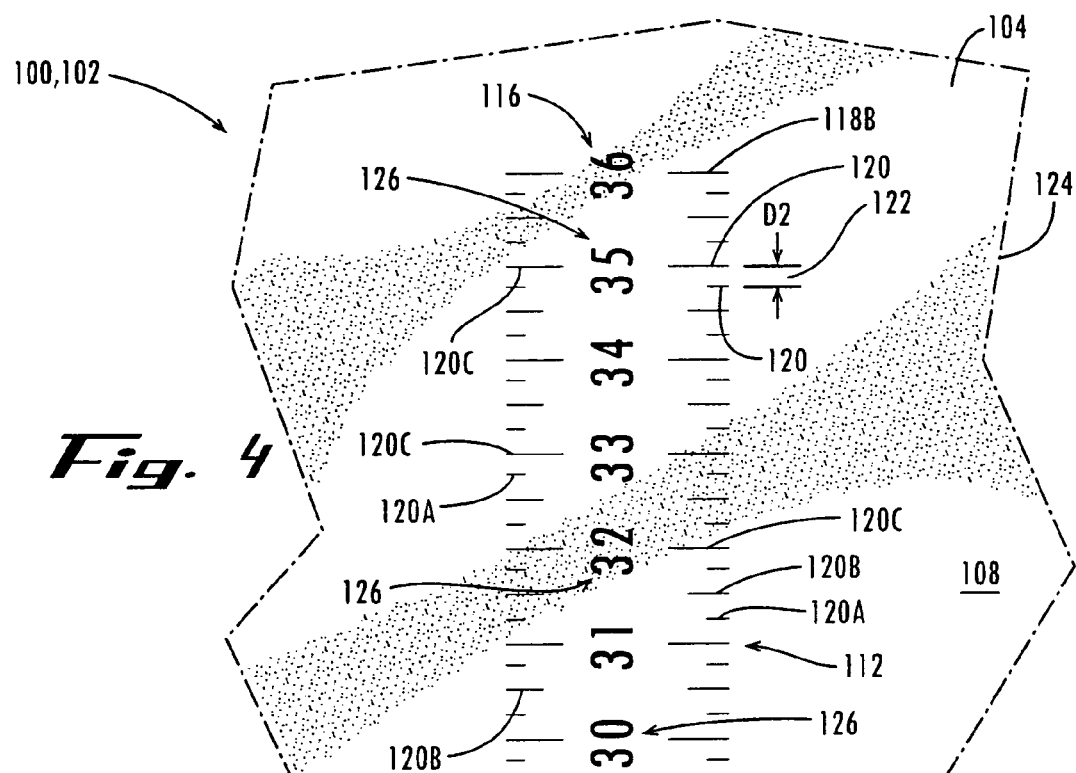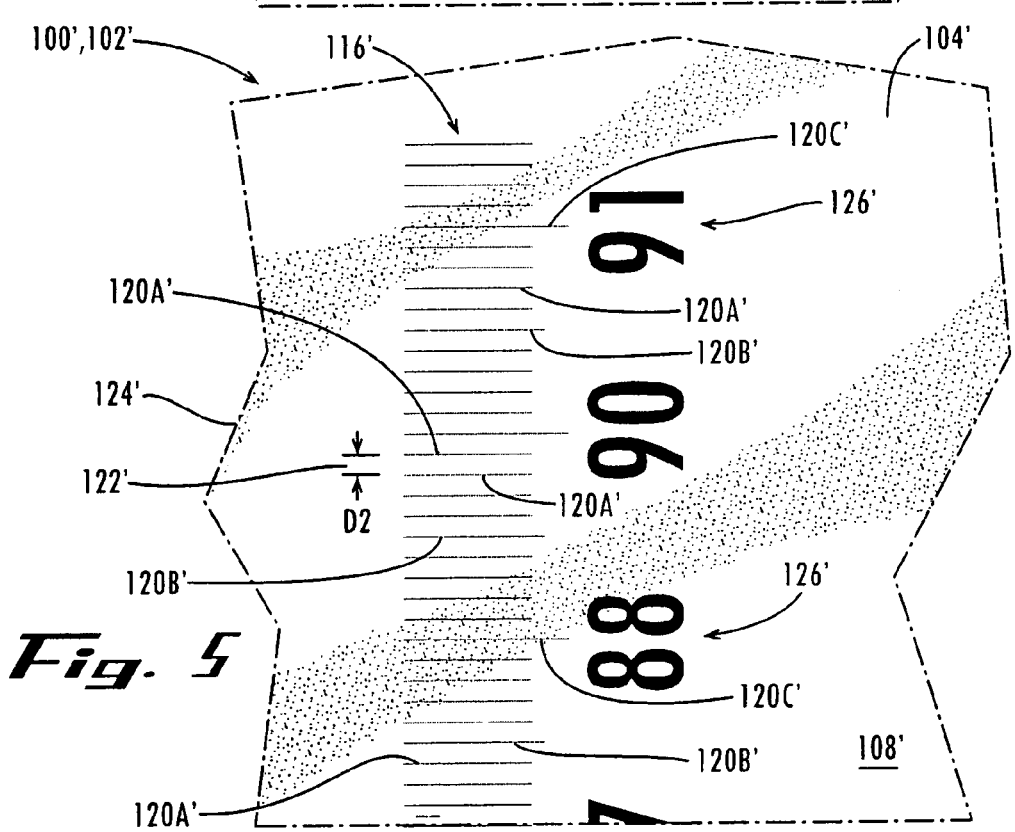

MEASURING BEDDING ARTICLES AND METHODS FOR MEASURING USING SAME

FIELD OF THE INVENTION

The present invention relates, generally, to the fields of bedding articles and measuring devices and, more specifically, to bedding articles and methods for measuring at least a portion of a human body.

BACKGROUND OF THE INVENTION

Human physical development is often monitored and tracked through the use of body measurements such as height and weight. Shortly after birth, a child's height (e.g., length) and weight are measured and recorded for many reasons, including for use as initial metrics or data points. Thereafter and as the child gets older, subsequent measurements are made of the child's height and weight and are compared against the initial metrics and other prior similar measurements to assess the child's physical development.

Traditionally, such height measurements have been made of an infant child through use of a tape measure, yardstick, meter stick, or other similar measuring device having markings thereon at regular units of distance and numerals associated with some such markings. To measure the child's height, the measuring device is generally positioned adjacent to the child when the child is lying in a prone position and with the top of the child's head located adjacent to the first marking at one of the measuring device's ends. A second marking nearest the bottom of one of the child's feet is identified and then the child's height is determined based on the distance between the first and second markings.

Once a child becomes able to stand upright, the child's height may be measured, for example, at a doctor's office using a medical scale adapted for such purpose. At home, the child's height may be measured by having the child stand on a floor near a wall and by making a mark on the wall corresponding to a horizontal plane passing immediately above the top of the child's head. Then, a measuring device such as a tape measure, yardstick, meter stick, or ruler is employed to determine the distance between the floor and the mark on the wall. The determined distance corresponds to the child's height.

Unfortunately, the foregoing methods of measuring a child's height require the use of a measuring device that may not be readily available at the time that a measurement is to be made. Also, if the child is an infant, only certain types of measuring devices may be safely used to measure the child's height as measuring devices made of metal or having sharp corners/edges might harm the child if the child is struck by such a measuring device in a vulnerable location. Additionally, if the child is an infant, the child's height is generally recorded in a notebook, on a form, or on a paper that may become readily separated from the child, misplaced, or lost.

Therefore, there exists in the industry, a need for a measuring device for measuring a child's height or a portion of a child's body that is particularly adapted for safely measuring an infant, and that addresses the above described, and other, problems, difficulties, and/or shortcomings of current apparatuses and methods.

SUMMARY OF THE INVENTION

Broadly described, the present invention comprises a measuring bedding article and methods for measuring the length of a person (e.g., a person's height) or a portion of a person's body. The present invention further comprises a measuring bedding article and methods for measuring the length of a child (e.g., a child's height) or a portion of a child's body generally, but not necessarily, while the child is lying down. The measuring bedding article may be embodied in a plurality of forms including, without limitation, a measuring blanket and a measuring crib sheet. Each measuring bedding article includes a measuring aid that enables measurements of a person's body to be made, for example, by a parent, caregiver, or other person. The measuring aid typically includes two end markings that define a total distance and a plurality of markings between the end markings that define distance increments, or subdivisions, of the total distance. Certain of the markings are associated in one-to-one correspondence with a numeral or other indicia that indicates a measure of distance and the renders the measuring aid (and, hence, the measuring bedding article) more usable for making measurements. In some exemplary embodiments, the measuring aid implements the English system of measure and units. In other exemplary embodiments, the measuring aid implements the metric system of measure and units. In still other exemplary embodiments, the measuring aid implements both the English and metric systems of measure and units.

The measuring bedding article may optionally further comprise a recordation label attached thereto or recordation area thereof for the recordation of measurements and dates associated with such measurements. The measuring bedding article and its recordation label or area are, in exemplary embodiments, manufactured from one or more materials that are receptive to printing and/or writing thereon with an indelible substance (such as, for example and not limitation, a permanent, non-toxic ink, other ink, or ink-like substance) and that retain such printing and/or writing without fading, smearing, smudging, or transfer thereof over time and through numerous washings and/or dry cleanings. In some exemplary embodiments, the measuring aid is printed directly on the measuring bedding article using a process including, but not limited to, screen-printing.

According to methods of the present invention, the measuring bedding article is generally laid on a flat, horizontal surface and spread out such that the measuring bedding article and its measuring aid are relatively taught. Then, a person to be measured is laid on the measuring bedding article. In some methods, the person is laid with at least a portion of his/her body on the measuring aid. In other methods, the person is laid with his/her body substantially adjacent and parallel to the measuring aid. Typically, in most methods of the present invention, the person is positioned such that a starting point of the body portion to be measured is aligned with an end of the measuring aid. For example, if a person's entire body length (e.g., the person's height) is to be measured, then the person is generally positioned with the top of his/her head aligned with an end of the measuring aid. Once the person is so positioned, the body portion is outstretched and then a marking nearest an ending point of the body portion to be measured is identified. If again, for example, the person's entire body length is to be measured, then the person's legs are outstretched, or straightened, and a marking nearest the bottom of one of the person's feet is identified. Then, a measurement of the body portion is determined using the distance increment nearest the identified marking and, generally, the numerals or other indicia associated with certain of the measuring aid's markings. After the measurement is made, it may be recorded by writing it and, perhaps, the corresponding date of the measurement on the recordation label or area with, for example, an indelible, non-toxic substance such as non-toxic ink. Alternatively, the measurement may be recorded by writing the measurement and corresponding date of the measurement directly on the measuring bedding article or by writing the corresponding date of the measurement directly on the measuring bedding article adjacent to the article's measuring aid.

Advantageously, the measuring bedding article enables the measurement of a person's body or portion thereof while the person is lying down, thereby allowing the measuring of children or infants who cannot yet stand or the measuring of adults or adolescents who may be unable to stand for some reason. The measuring bedding article also enables such measurements to be made without the use of a measuring device that might not be available at a time when the making of a measurement is desired or that might have sharp corners, edges, or other portions that might cause injury to the person being measured. Additionally, the measuring bedding article allows a record of body measurements and/or their corresponding dates to made, associated, and maintained therewith and, therefore, eliminates the possibility that such measurements and/or corresponding dates may become misplaced or lost. By virtue of the measuring bedding article's ability to record and maintain measurements and their corresponding dates, a parent, caregiver, or other person can review the measurements and their dates and assess the physical development or, in the case of older person, the physical decline of a person. Further, because the measuring bedding article may be embodied as a measuring blanket, the measuring bedding article may be used to keep a person warm and, for infants or small children, to wrap them up or swaddle them.

Other advantages and benefits of the present invention will become apparent upon reading and understanding the present specification when taken in conjunction with the appended drawings.

BRIEF DESCRIPTION OF THE DRAWINGS

FIG. 4 displays a partial top plan view of the measuring bedding article of FIG. 1 showing a portion of a measuring aid thereof.

FIG. 5 displays a partial top plan view of a measuring bedding article, in accordance with a second exemplary embodiment of the present invention, showing a portion of a measuring aid thereof.

FIG. 7 displays a bottom perspective view of the measuring bedding article of FIG. 1.

DETAILED DESCRIPTION OF THE DRAWINGS

Figure 1:
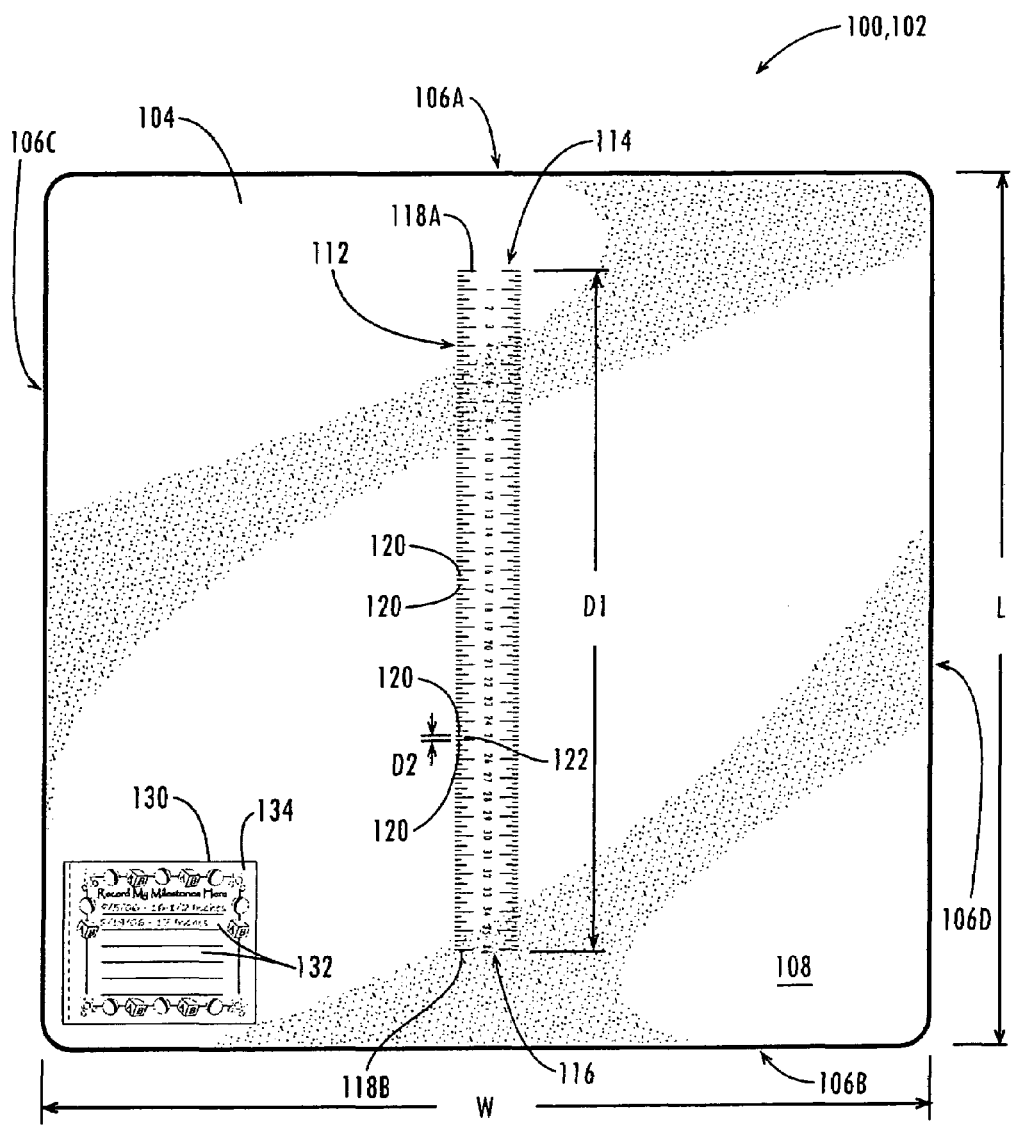
FIG. 1 displays a top plan view of a measuring bedding article in accordance with a first exemplary embodiment of the present invention.
Figure 2:
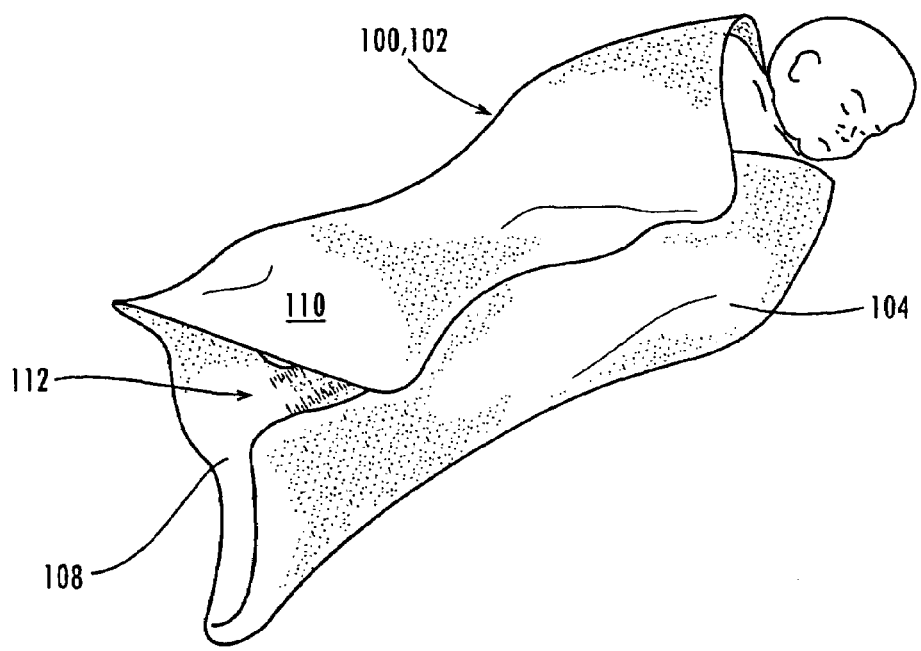
FIG. 2 displays a top perspective view of the measuring bedding article of FIG. 1 during use thereof to swaddle a child.

Referring now to the drawings in which like numerals represent like elements or steps throughout the several views, FIG. 1 displays a top plan view of a measuring bedding article 100 in accordance with a first exemplary embodiment of the present invention. More specifically, the measuring bedding article 100 is embodied in the first exemplary embodiment as a measuring blanket 102 for a child (generally, but not limited to, an infant) that keeps the child warm and that is usable by a parent, caregiver, or other person to measure the length of the child's body (e.g., the child's height) or to measure only a portion of the child's body. For example, a child may be placed under the measuring blanket 102 to keep the child warm when the child is lying down during rest or sleep. A child may also be wrapped up or swaddled in the measuring blanket 102 when the child is to be carried, held, or moved about as illustrated in FIG. 2. In further example, a child may be laid upon the measuring blanket 102 by a parent, caregiver, or other person, as described in more detail below with reference to FIGS. 8 and 9, to measure the length of the child's body or another portion of the child's body such as the length, width, or circumference of, for instance, the child's head, chest, waist, hips, arms, legs, fingers, or toes. It should be noted that in order to perform such a circumference measurement, the measuring blanket 102 may be wrapped around the portion of the child's body to measured. It should also be noted that although measuring bedding articles 100 are described herein with reference to exemplary embodiments thereof directed to children, the measuring bedding articles 100 may be used in connection with adolescents or adults as well.

Figure 3:
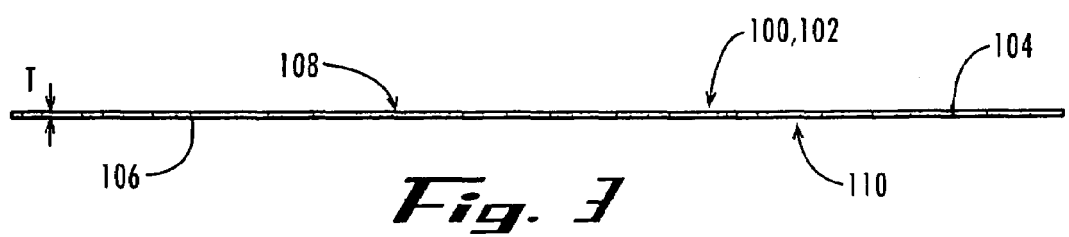
FIG. 3 displays an edge view of the measuring bedding article of FIG. 1.

The measuring blanket 102, as illustrated in FIG. 1, comprises a sheet-like member 104 elongated in multiple directions and having a plurality of edges 106 that extend around the member 104 and define the boundary or limit thereof. The member 104 generally has a rectangular shape having a length, L, and a width, W, but may have a different shape in another exemplary embodiment. As seen more clearly in the edge view of FIG. 3, the member 104 also has a thickness, T, which is typically relatively small in comparison to the member's 104 length or width. In an exemplary embodiment, member 104 may have a length, L, of 40 inches, a width, W, of 30 inches, and a thickness, T, of $\frac{1}{8}^{th}$ of an inch, but member 104 may be of any size that accommodates a desired measuring aid 112 (described below). Generally, the member 104 is manufactured from a single ply of soft material that is selected to keep a child warm when the child resides on or under the measuring blanket 102 or is wrapped up therewithin, but that is flexible enough for wrapping or swaddling the child therein. The member 104 is also generally manufactured from a material selected so as to be durable enough to withstand the conditions of use to which it will be exposed during use and to withstand repeated washings and/or dry cleanings. Additionally, the member 104 is usually manufactured from a material that accepts or is receptive to printing thereon with an appropriate indelible, non-toxic substance (ink, ink-like, or other substance) and that retains such printing without fading, smearing, smudging, or transfer thereof over time and through numerous washings and/or dry cleanings. The member 104 may be manufactured, for example, from woven or non-woven fabrics or paper, but may be manufactured from other fabrics and/or materials and with one or more plies of such other fabrics and/or materials.

Additionally, the member 104 has a first side 108 (see FIG. 1) and an opposed second side 110 (see FIG. 7). The first side 108 has a measuring aid 112 that is used by a parent, caregiver, or other person to make measurements of a child's body. The measuring aid 112 generally resembles the markings present on a yardstick, meter stick, ruler, or tape measure and may utilize the English system of measure (see FIGS. 1 and 4), the metric system of measure (see FIG. 5), or both the English and metric systems of measure (see FIG. 6). Although shown partially extending between two opposed edges 106A, 106B of the member 104 in FIG. 1 and substantially perpendicular to opposed edges 106C, 106D, the measuring aid 112 may be oriented in any direction or angle relative to the edges 106 of the member 104 and may be of any length. The measuring aid 112 is typically printed on the first side 108 of the member 104 using an indelible, non-toxic substance (ink, ink-like, or other substance) that is selected in combination with the material of the member 104 to resist, as noted above, fading, smearing, smudging, or transfer thereof over time and through numerous washings and/or dry cleanings. Generally, the indelible non-toxic substance is applied to the member 104 by a printing process including, but not limited to, a screen-printing process. The measuring aid 112 may also be applied to or formed on member 104 by other processes such as, for example and not limitation, embroidery, iron on transfer, heat stamp transfer, airbrushing, stenciling, or other similar processes.

The measuring aid 112 has a first end 114 and an opposed second end 116 located distant therefrom. According to a first exemplary embodiment of the present invention, the measuring aid 112 has a first marking 118A located at or proximate the measuring aid's first end 114 and a second marking 118B located at or proximate the measuring aid's second end 116. The first and second markings 118A, 118B are separated by a distance, D1, and generally the first marking 118A is located at the "zero" end of the measuring aid 112. Typically, the distance, D1, is selected to correspond with a standard unit of measure for the system of measure (e.g., the English and/or metric systems) employed by the measuring aid 112. Thus, for example and not limitation, if the measuring aid 112 utilizes the English system of measure, then the distance, D1, may equal one yard or 36 inches. Similarly, if the measuring aid 112 utilizes the metric system of measure, then the distance, D1, may equal one meter or 100 centimeters. Alternatively, the distance, D1, may be greater than or less than a yard or meter, as appropriate or as desired.

Figure 6:
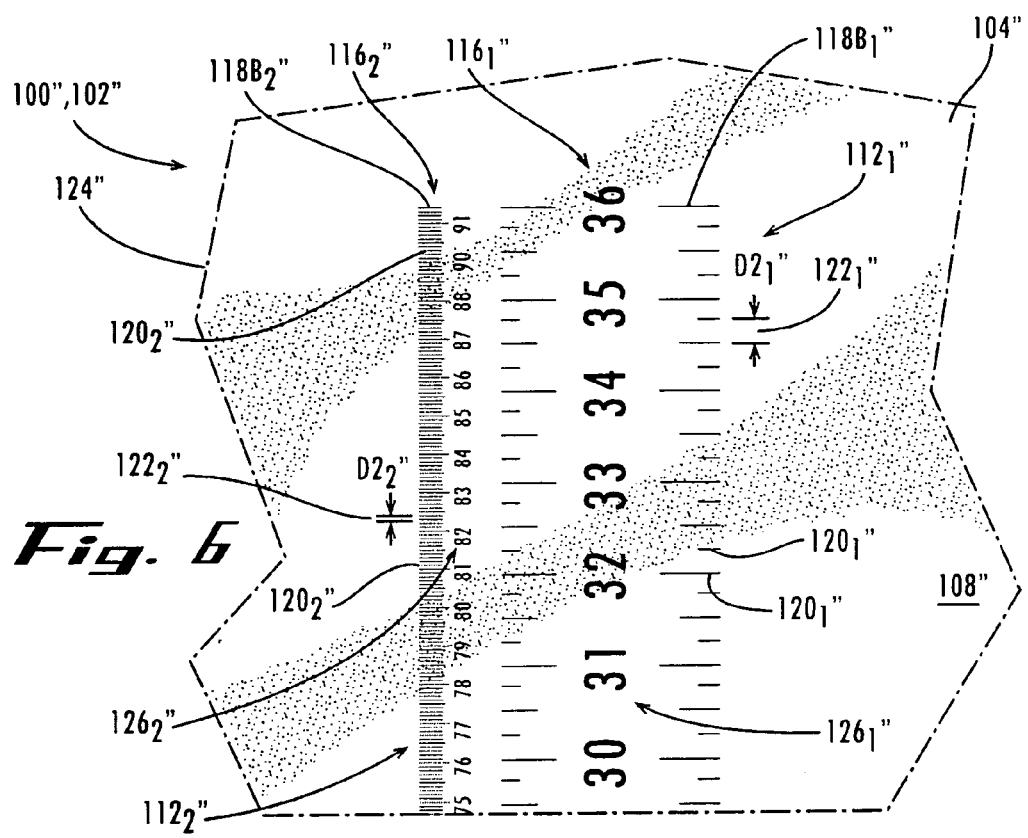
FIG. 6 displays a partial top plan view of a measuring bedding article, in accordance with a third exemplary embodiment of the present invention, showing a portion of a measuring aid thereof.

Between the first and second markings 118A, 118B and as seen more clearly in FIGS. 4-6, the measuring aid 112 includes a plurality of markings 120 that subdivide the distance, D1, into a plurality of distance increments 122. Each distance increment 122 is bounded by two of the markings 120 and defines a distance, D2, which generally corresponds to a standard unit of measure for the system of measure used by the measuring aid 112. Therefore, for example, each distance increment 122 corresponds to and defines a distance, D2, of an eighth of inch, a quarter of an inch, a half of an inch, an inch, a millimeter, a half of a centimeter, a centimeter, or other desirable distance or unit of measure, depending on the particular system of measure employed by the measuring aid 112. It should be noted, however, that the distance increment 122 utilized in a particular exemplary embodiment of the present invention may also be selected for other practical reasons such as manufacturing considerations, the ability of humans to read measurements, and the degree of accuracy or fidelity required for measurements. Thus, in the first exemplary embodiment and as illustrated in FIGS. 1 and 4, each pair of adjacent markings 120 defines a distance increment 122 therebetween of one quarter of an inch as it is believed that measurements having an accuracy of more than one quarter of an inch may not be necessary. Furthermore, it may not be realistic to attempt to make measurements with more accuracy when, often times, a child being measured will be moving around substantially during the measurement process.

FIG. 2 displays a top perspective view of the measuring bedding article 100 of FIG. 1 during use thereof with a child wrapped up or swaddled in the measuring bedding article 100. As seen in FIG. 2, the child's body is substantially adjacent the first side 108 of member 104 with the measuring aid 112 being partially visible. The second side 110 of member 104 is exposed to the surroundings.

FIG. 4 displays a partial top plan view of the measuring bedding article 100 of FIG. 1, in accordance with a first exemplary embodiment of the present invention, showing a portion 124 thereof. The portion 124 of the measuring bedding article 100 (and, hence, of the measuring blanket 102) includes the measuring aid's second end 116 and a part of the measuring aid 112 extending toward the first end 114 thereof. As illustrated in FIG. 4, the measuring aid 112 employs the English system of measure with markings 120 that subdivide the distance, D1, of the measuring aid 112 into a plurality of distance increments 122 each defining a distance, D2, equal to one quarter of an inch. Also, as seen in FIG. 4, markings 120A at quarter-inch locations, markings 120B at half-inch locations, and markings 120C at inch locations each have a different length so as to make the measuring aid 112 more easily read by a human. Additionally, the measuring aid 112 further comprises a plurality of numerals 126 associated respectively with markings 120C such that each numeral 126 corresponds in one-to-one correspondence with a marking 120C and identifies the number of inches between such marking 120C and the measuring aid's first end 114. The presence of numerals 126 renders the making of measurements easier by eliminating the need for a parent, caretaker, or other person to count the number of markings 120C from the measuring aid's first end 114 while making a measurement.

As described briefly above and as illustrated in FIG. 5, the measuring bedding article 100' includes a measuring aid 112' that utilizes the metric system of measure in accordance with a second exemplary embodiment of the present invention substantially similar to the first exemplary embodiment. FIG. 5 displays a partial top plan view of such measuring bedding article 100' (and, hence, of such measuring blanket 102') showing a portion 124' thereof that includes the measuring aid's second end 116' and a part of the measuring aid 112' extending toward the first end 114' thereof. The measuring aid 112' of FIG. 5 defines a distance, D1', of one meter (i.e., 39.37 inches) and has markings 120' that subdivide distance, D1', into a plurality of distance increments 122' each defining a distance, D2', equal to one millimeter. Similar to the measuring aid 112 of FIG. 4, the measuring aid 112' of FIG. 5 has markings 120A' at millimeter locations, markings 120B' at one-half centimeter locations, and markings 120C' at centimeter locations that have different lengths to improve the readability of the measuring aid 112'. Further, the measuring aid 112 of FIG. 5 comprises a plurality of numerals 126' that are associated in one-to-one correspondence with markings 120C' and that identify, for each such marking 120C', the number of centimeters between the marking 120C' and the first end 114' of the measuring aid 112'. By virtue of its use of distances D1' and D2', markings 120', distance increments 122', and numerals consistent with the metric system of measure, the measuring blanket 102' of FIG. 5 is usable by persons who are more familiar with or prefer to use the metric system of measure such as, for example and not limitation, persons residing in European countries.

FIG. 6 provides a partial top plan view of a measuring bedding article 100", according to a third exemplary embodiment of the present invention that is substantially similar to the first and second exemplary embodiments described herein, showing a portion 124" thereof. As seen in FIG. 6, the measuring bedding article 100 (and, hence, the measuring blanket 102") includes a first measuring aid $112_1"$ that utilizes the English system of measure with distances $D1_1"$ and $D2_1"$, markings $120_1$, distance increments $122_1$, and numerals $126_1$ similar to those of the measuring blanket 102 of FIGS. 1 and 4. However, the measuring blanket 102" of FIG. 6 also includes a second measuring aid $112_2"$ that employs the metric system of measure with distances $D1_2"$ and $D2_2"$, markings $120_2"$, distance increments $122_2"$, and numerals $126_2"$ similar to those of the measuring blanket 102' of FIG. 5. The first measuring aid $112_1"$ is substantially adjacent and parallel to the second measuring aid $112_2"$, thereby enabling a measurement to be readily made using either one or both of the English and/or metric systems of measure. Such a measuring blanket 102" may be used by persons who are familiar with both the English and metric systems of measure or who travel through or reside part-time in countries that use either of such systems of measure.

The members 104 of each of the measuring bedding articles 100 of the various exemplary embodiments described herein, as noted above, also have a second side 110. As illustrated in the bottom perspective view of FIG. 7, the second side 110 of member 104 has one or more decorative elements 128. Such decorative elements 128 are selected to improve the measuring bedding articles' attractiveness or aesthetic appeal and may, but not necessarily, be selected for their association with or attraction to children. The decorative elements 128 may be applied to or formed on a member 104 by processes such as, for example and not limitation, screen-printing, embroidery, iron on transfer, heat stamp transfer, airbrushing, stenciling, or other similar processes. Alternatively, the decorative elements 128 may comprise designs made of fabric sewn or otherwise attached to members 104. The decorative elements 128 may also comprise a design woven into or otherwise incorporated into the material of the members' second sides 110.

Figure 8:
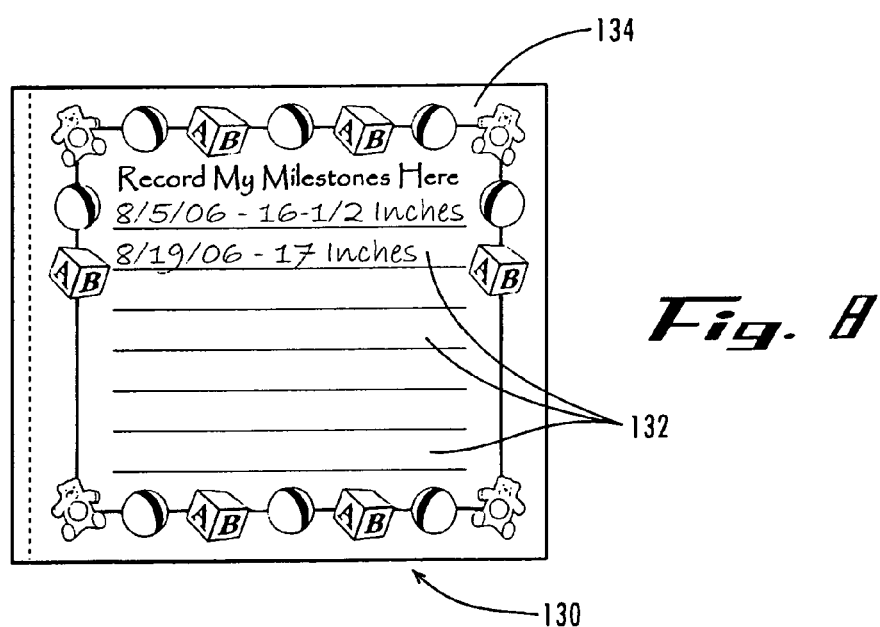
FIG. 8 displays a top plan view of a recordation label of the measuring bedding article of FIG. 1.
Figure 1:
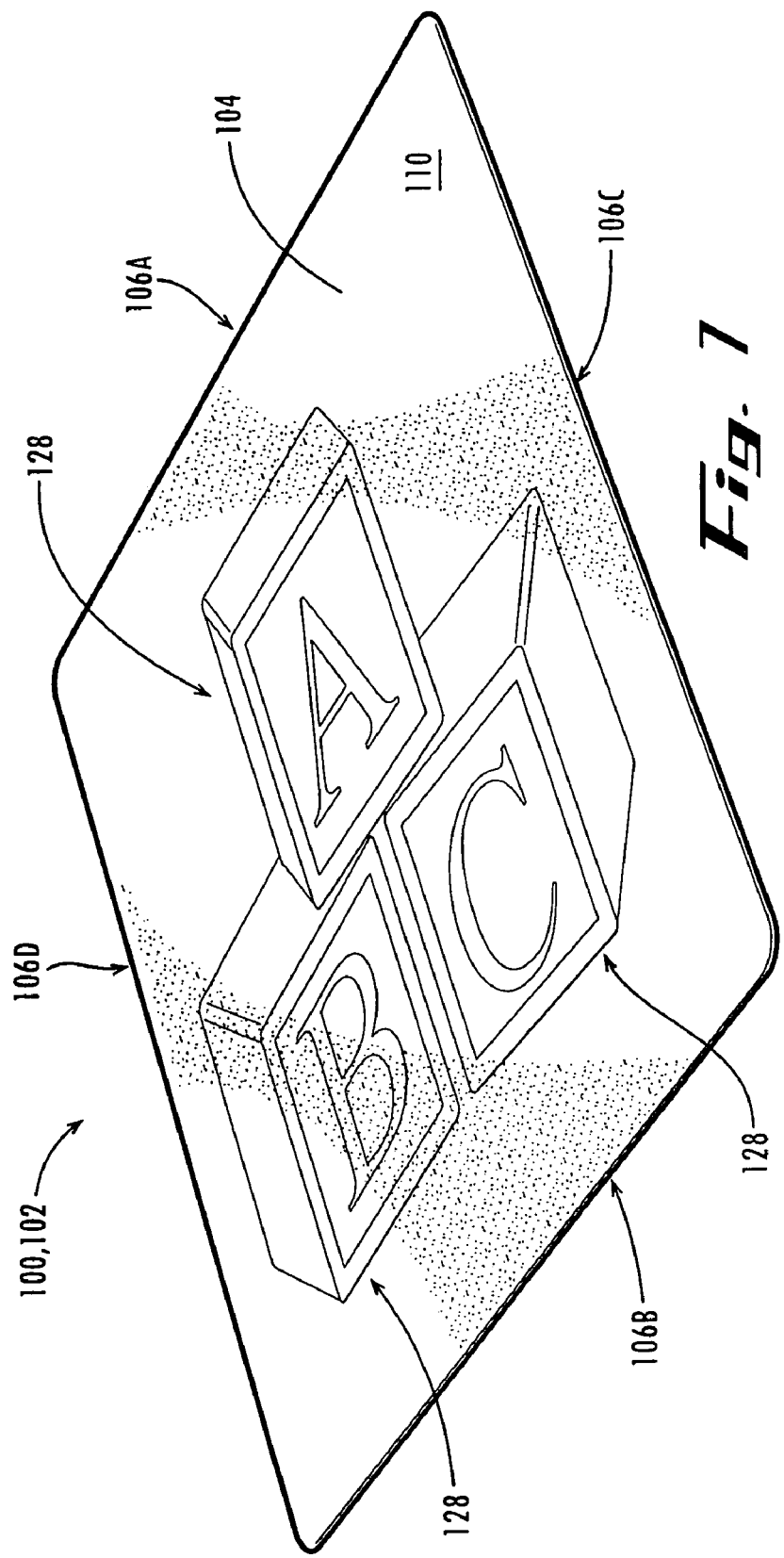

Before describing exemplary methods of using a measuring bedding article 100, it should be noted that the measuring bedding articles 100 of the exemplary embodiments generally further comprise a recordation label 130 affixed to members 104 thereof. The recordation label 130, as illustrated more visibly in FIG. 8, include a plurality of locations 132 thereon for a parent, caregiver, or other person to record, in writing and over time, multiple measurements of the length of a child's body or portion of the child's body. Conveniently, such measurements may be made through use of the measuring bedding articles 100. Thus, as illustrated in FIG. 8, when a first measurement of the length of a child's body (e.g., the child's height) is made, the person performing such measurement may enter, for example and not limitation, the length (e.g., in feet and/or inches) and the corresponding date (e.g., month, day, year) of the measurement at a first location 132A. Then, when subsequent measurements of the length of the child's body are made, the person(s) performing such measurements may enter, for example, the length and the corresponding date of such measurements at other locations 132. By later reviewing the recorded measurements of the child's length and the corresponding dates written on the recordation label 130, one can assess the child's physical development and/or the rate thereof.

As illustrated in FIG. 8, the recordation label 130 is generally located near one or more edges 106 of a measuring bedding article 100. In some exemplary embodiments, the recordation label 130 comprises a sheet-like member 134 manufactured from a material that is selected so as to be durable enough to withstand the conditions to which it will be exposed during use and to withstand repeated washings and/or dry cleanings. Additionally, the member 134 is usually manufactured from a material that accepts or is receptive to printing and/or writing thereon with an appropriate indelible, non-toxic substance (or ink, ink-like, or other substance) and that retains such printing and/or writing without fading, smearing, smudging, or transfer thereof over time and through numerous washings and/or dry cleanings. The member 134 may be manufactured, for example, from woven or non-woven fabrics or paper, but may be manufactured from other fabrics and/or materials and with one or more plies of such other fabrics and/or materials. The member 134 is typically attached to a member 104 of a measuring bedding article 100 by sewing. Generally, a pen or other similar implement having an indelible, non-toxic substance (such as, for example, a fabric pen) is utilized by person(s) to record measurements and corresponding dates (e.g., measurement-related information or data) on member 134.

In other exemplary embodiments, the recordation label 130 is formed directly on a measuring bedding article 100 by printing the recordation label 130 and its plurality of locations 132 on members 104 using, for example and not limitation, an indelible, non-toxic substance (ink, ink-like, or other substance) and a process such as screen-printing. In such exemplary embodiments, a person(s) may record measurements and corresponding dates on the recordation label 130 by writing directly on the measuring bedding article 100. Similar recordation labels 130 may be formed on or integral with a member 104 by processes such as, for example and not limitation, embroidery, iron on transfer, heat stamp transfer, airbrushing, stenciling, or other similar processes.

It should be noted that in addition to recording measurements pertaining to a child and the corresponding dates thereof on a recordation label 130, such measurements and dates may be written directly on a measuring bedding article 100. Also, measurements recorded directly on a measuring bedding article 100 may not include a numerical value, but may instead include a mark and/or date made adjacent or relative to a marking 120 of a measuring bedding article 100.

Figure 9:
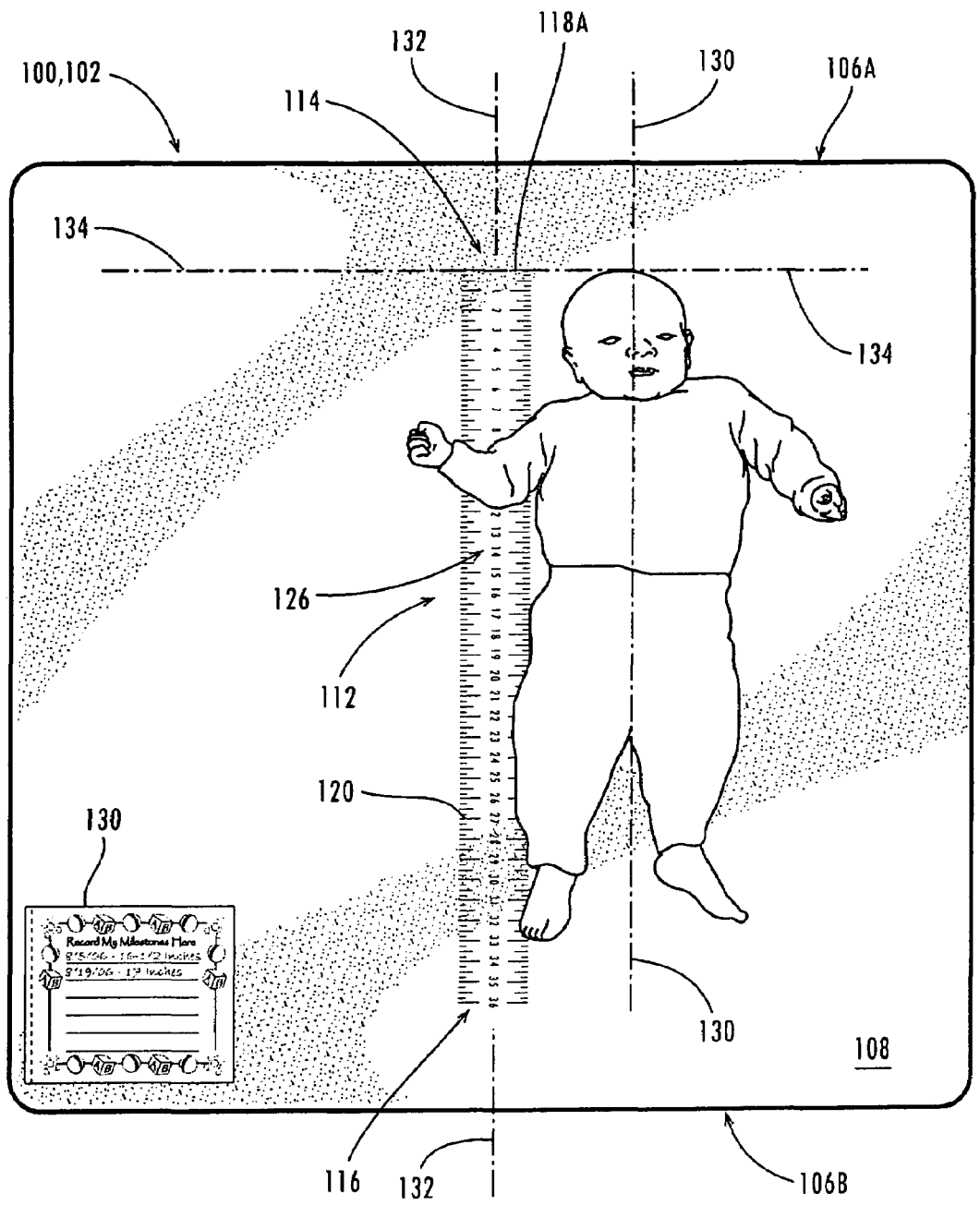
FIG. 9 displays a top plan view of the measuring bedding article of FIG. 1 during use thereof to make a measurement of a child according to a first exemplary method.

FIG. 9 displays a top plan view of a measuring bedding article 100 in the form a measuring blanket 102 during use thereof to make a measurement of the length of a child's body according to first exemplary method. As depicted in FIG. 9, the measuring blanket 102 is laid on a substantially flat, horizontal surface such that the portion of the measuring blanket 102 between opposing edges 106A, 106B and measuring aid 112 are substantially taught. Then, a child's body is laid on top of the measuring blanket 102 with the child's body present at least partially on and at least partially in contact with the measuring aid 112 such that a longitudinal axis 130 of the child's body is substantially parallel to a longitudinal axis 132 extending through the measuring aid's ends 114, 116. When placed on the measuring blanket 102, the top of the child's head is positioned substantially parallel to or even with marking 118A of the measuring aid 112. In such position, a plane 134 perpendicular to the longitudinal axis 132 of the measuring aid 112 and substantially perpendicular to the longitudinal axis 130 of the child's body barely touches the top of the child's head and passes through marking 118A (i.e., through the "zero" end) of the measuring aid 112. Next, the child's legs are straightened out as much as possible and a marking 120 nearest the bottom of one of the child's feet is identified. The distance between marking 118A and the identified marking 120 is then determined (for example, at least partially through the use of numerals 126). The determined distance corresponds to the length of the child's body.

Figure 10:
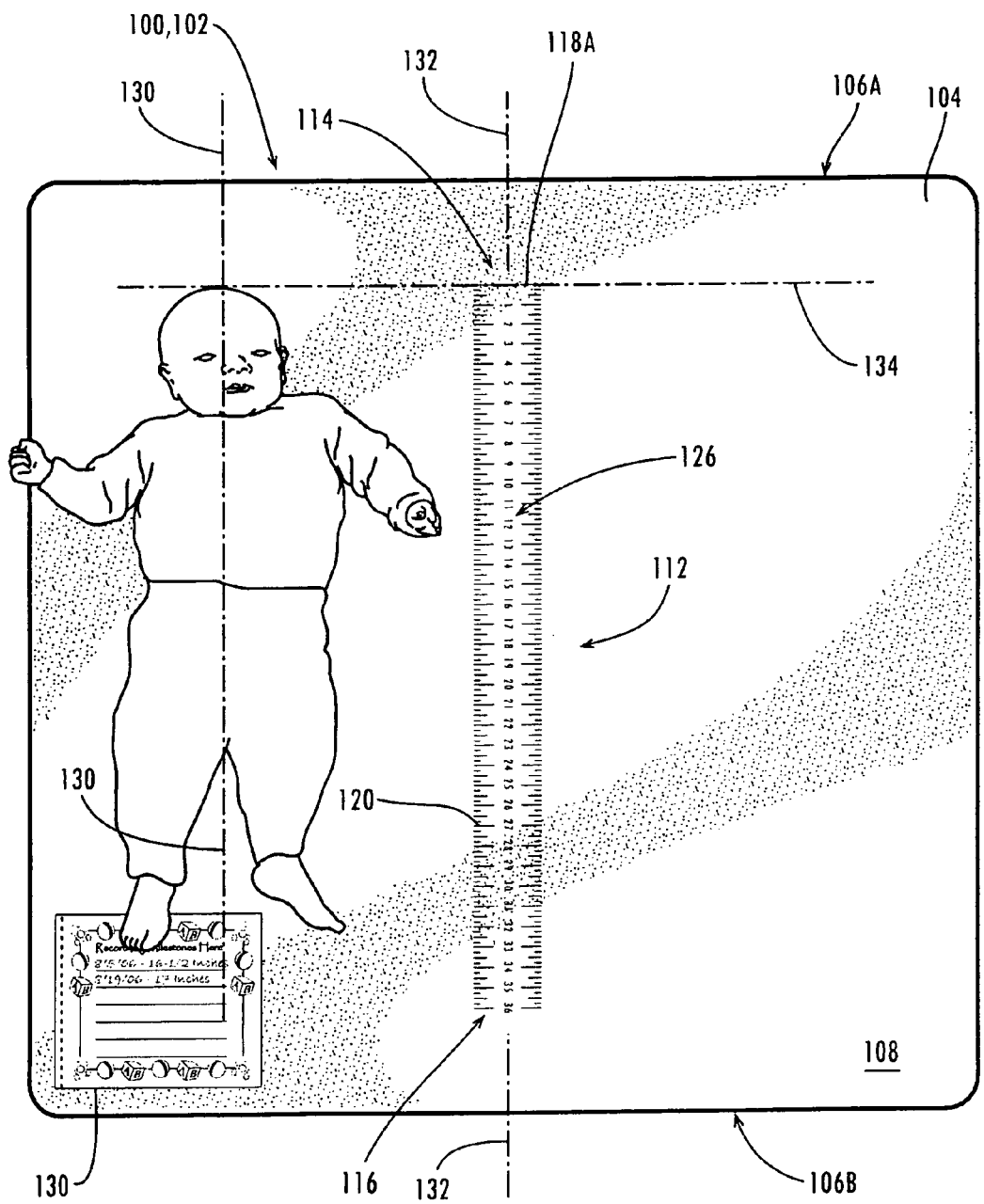
FIG. 10 displays a top plan view of the measuring bedding article of FIG. 1 during use thereof to make a measurement of a child according to a second exemplary method.

FIG. 10 displays a top plan view of a measuring bedding article 100 in the form of a measuring blanket 102 during use thereof, in accordance with a second exemplary method, to measure the length of a child's body. Similar to the first exemplary method described above, the measuring blanket 102 is laid on a substantially flat, horizontal surface such that the portion of the measuring blanket 102 between opposing edges 106A, 106B and measuring aid 112 are substantially taught. However, instead of laying a child's body at least partially on the measuring aid 112 as in the first exemplary method, the child's body is placed substantially adjacent and parallel to the measuring aid 112 such that a longitudinal axis 130 of the child's body is substantially parallel to a longitudinal axis 132 extending through the measuring aid's ends 114, 116. When so placed on the measuring blanket 102, the top of the child's head is positioned substantially parallel to or even with marking 118A of the measuring aid 112. In such position, a plane 134 perpendicular to the longitudinal axis 132 of the measuring aid 112 and substantially perpendicular to the longitudinal axis 130 of the child's body barely touches the top of the child's head and passes through marking 118A (i.e., through the "zero" end) of the measuring aid 112. Similar to the first exemplary method described above, the child's legs are next straightened out as much as possible and a marking 120 nearest the bottom of one of the child's feet is identified. The distance between marking 118A and the identified marking 120 is then determined (for example, at least partially through the use of numerals 126). The determined distance corresponds to the length of the child's body. By the child's body not being placed at least partially on the measuring aid 112, the markings 120 of the measuring aid 112 are more readily visible and, therefore, the identification of a marking 120 nearest the bottom of one of the child's feet is more easily made.

Figure 11:
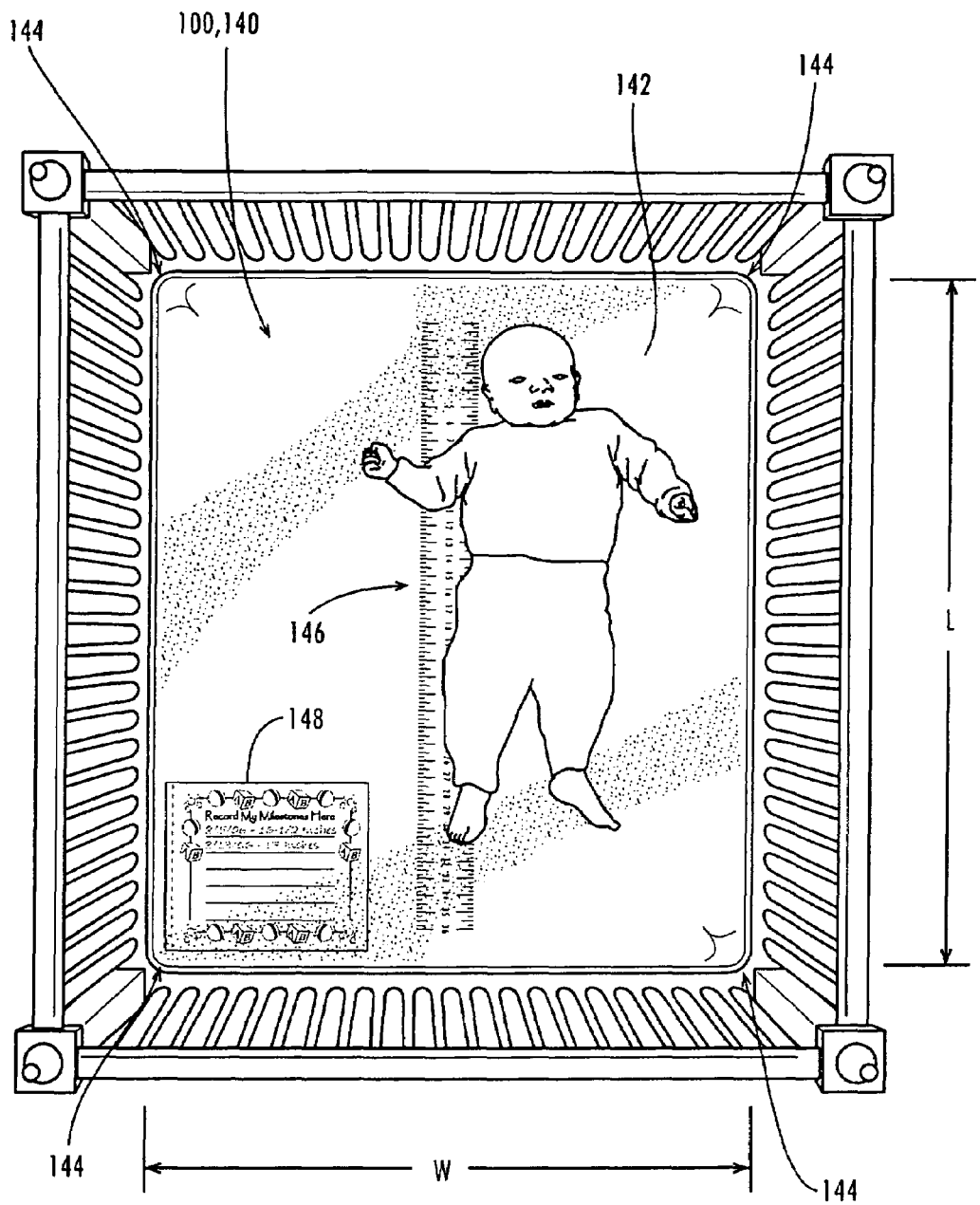
FIG. 11 displays a top plan view of a measuring bedding article in accordance with a fourth exemplary embodiment of the present invention.

FIG. 11 displays a top plan view of another measuring bedding article 100 in accordance with a fourth exemplary embodiment of the present invention. The measuring bedding article 100 is embodied in the fourth exemplary embodiment as a measuring crib sheet 140 for a child (generally, but not limited to, an infant) that covers a crib's mattress and provides a comfortable surface for the child to lie on when present in a crib. The measuring crib sheet 140 is similar to a measuring blanket 102 and, therefore, using methods similar to those described herein with respect to a measuring blanket 102, may be used by a parent, caregiver, or other person to measure the length of the child's body (e.g., the child's height) or to measure only a portion of the child's body.

The measuring crib sheet 140, similar to a measuring blanket 102, comprises a sheet-like member 142 elongated in multiple directions and having a plurality of corners 144 with elastic therein that removably secure the member 142 in position at least partially covering a crib's mattress. The member 142 generally has a rectangular shape having a length, L, and a width, W, but may have a different shape in another exemplary embodiment. Typically, the length, L, and width, W, are selected so that the measuring crib sheet 140 fits and may be used in conjunction with standard size crib mattresses.

Member 142 is generally manufactured from a single ply of soft material that is selected to provide a child with comfort while laying on the measuring crib sheet 140 and to be flexible (and, perhaps, somewhat stretchable) enough for ease of installation on a crib's mattress. The member 142 is also generally manufactured from a material selected so as to be durable enough to withstand the conditions of use to which it will be exposed and to withstand repeated washings and/or dry cleanings. Additionally, the member 142 is usually manufactured from a material that accepts or is receptive to printing thereon with an appropriate indelible, non-toxic substance (ink, ink-like, or other substance) and that retains such printing without fading, smearing, smudging, or transfer thereof over time and through numerous washings and/or dry cleanings. The member 142 may be manufactured, for example, from woven or non-woven fabrics or paper, but may be manufactured from other fabrics and/or materials and with one or more plies of such other fabrics and/or materials.

The member 142 includes a measuring aid 146 that is substantially similar to the measuring aid 112 of the measuring blanket 102 described above and that is used to make measurements of a child using methods similar thereto. The member 142 also generally includes a recordation label 148 or area substantially similar to that of the measuring blanket 102 described above. The recordation label 148 or area is used, like the recordation label 130 or area of the measuring blanket 102, to record measurements of a child and/or corresponding dates of such measurements.

Whereas the present invention has been described in detail above with respect to exemplary embodiments thereof, it should be understood that variations and modifications might be effected within the spirit and scope of the present invention, as described herein before and as defined in the appended claims.

What is claimed is:

1. A measuring bedding article for measuring at least a portion of a human body, said measuring bedding article comprising:

a member for use as bedding, said member comprising a single layer of a single material and having opposing edges, said single material being sufficiently flexible so as to enable wrapping of said member at least partially around a mattress of a bed;

a measuring aid present on said member for making distance-related measurements of at least a portion of a human body, said measuring aid having first and second ends with at least one end being located at a distance offset from one edge of said opposing edges of said member; and a recordation portion present on said member and adapted for recordation thereon of (i) measurement data pertaining to multiple distance-related measurements of at least a portion of a human body and (ii) date data associated respectively with said measurement data, wherein said measurement data and associated date data display changes over time in the size of said portion of said human body.

2. The measuring bedding article of claim 1, wherein said measuring aid includes a plurality of markings for making distance-related measurements, each adjacent pair of said markings defining a uniform distance therebetween.

3. The measuring bedding article of claim 1, wherein said measuring aid is printed on said member.

4. The measuring bedding article of claim 1, wherein said member comprises a first member and said measuring aid comprises a second member secured to said first member.

5. The measuring bedding article of claim 1, wherein said measuring aid comprises a transfer adhered to said member.

6. The measuring bedding article of claim 1, wherein said measuring aid is formed of thread secured to said member.

7. The measuring bedding article of claim 1, wherein said measuring aid is adapted for making a distance-related measurement of at least a portion of a human body when said portion of said human body is adjacent said member.

8. The measuring bedding article of claim 1, wherein said measuring aid is adapted for making said distance-related measurement of at least said portion of said human body when said portion of said human body is laid upon and in contact with said member.

9. The measuring bedding article of claim 1, wherein said measuring aid is configured for making a distance-related measurement of at least a portion of a human body using the English system of measure.

10. The measuring bedding article of claim 1, wherein said measuring aid is configured for making a distance-related measurement of at least a portion of a human body using the metric system of measure.

11. The measuring bedding article of claim 1, wherein said measuring aid is configured for making a distance-related measurement of at least a portion of a human body using the English and metric systems of measure.

12. The measuring bedding article of claim 1, wherein said member comprises a material selected to receive and maintain marking thereon of a date corresponding to a measurement of at least a portion of a human body.

13. The measuring bedding article of claim 1, wherein said member comprises a material selected to receive and maintain a mark made thereon corresponding to a measurement of at least a portion of a human body.

14. The measuring bedding article of claim 1, wherein said recordation portion comprises a label affixed to said member.

15. The measuring bedding article of claim 1 wherein said recordation portion is configured to receive said measurement data marked thereon with an indelible substance.

16. The measuring bedding article of claim 1, wherein said member comprises a blanket and said single layer of material is selected so as to keep a human warm.

17. The measuring bedding article of claim 1, wherein said member comprises a bed sheet.

18. A measuring bedding article for measuring at least a portion of a human body, said measuring bedding article comprising:
    a member for use on a bed as bedding and formed from a single ply of a single flexible material having first and second opposing edges, wherein said member comprises a plurality of markings located between a first end marking and a second end marking for making distance-related measurements, each adjacent pair of said markings of said plurality of markings defining a uniform distance therebetween, wherein said first end marking is offset by a distance from said first opposing edge with no markings for making distance-related measurements present between said first end marking and said first opposing edge; and
    a recordation area present on said member and adapted for recordation thereon of (i) distance-related measurement data pertaining to multiple distance-related measurements of a human body and (ii) date data associated respectively with said distance-related measurement data,
    wherein said distance-related measurement data and associated date data display changes over time in the size of said human body.

19. The measuring bedding article of claim 18, wherein said plurality of markings are permanently applied to said member.

20. The measuring bedding article of claim 18, wherein said member comprises a material that is adapted to receive and maintain measurement-related information marked thereon with an indelible substance absent substantial degradation over time.

21. The measuring bedding article of claim 18, wherein said member comprises a blanket.

22. The measuring bedding article of claim 18, wherein said member comprises a bed sheet.

23. The measuring bedding article of claim 18, wherein said human body comprises a child's body.

* * * * *